United States Patent
Chedid et al.

(10) Patent No.: US 8,455,693 B2
(45) Date of Patent: Jun. 4, 2013

(54) PROCESS FOR PREPARING 2-(2-TERT-BUTYLAMINOETHOXY)ETHANOL (TERT-BUTYLAMINODIGLYCOL, TBADG)

(75) Inventors: Roland Bou Chedid, Mannheim (DE); Johann-Peter Melder, Böhl-Iggelheim (DE); Steven Brughmans, Mannheim (DE); Torsten Katz, Neustadt (DE)

(73) Assignee: BASF SE (DE)

( * ) Notice: Subject to any disclaimer, the term of this patent is extended or adjusted under 35 U.S.C. 154(b) by 123 days.

(21) Appl. No.: 13/112,161

(22) Filed: May 20, 2011

(65) Prior Publication Data

US 2011/0288337 A1  Nov. 24, 2011

Related U.S. Application Data

(60) Provisional application No. 61/346,923, filed on May 21, 2010, provisional application No. 61/407,467, filed on Oct. 28, 2010.

(51) Int. Cl.
   *C07C 209/16* (2006.01)
(52) U.S. Cl.
   USPC .................... 564/479; 564/474; 564/480
(58) Field of Classification Search
   None
   See application file for complete search history.

(56) References Cited

U.S. PATENT DOCUMENTS

| | | |
|---|---|---|
| 4,386,219 A | 5/1983 | Merger et al. |
| 4,405,585 A | 9/1983 | Sartori et al. |
| 4,487,967 A | 12/1984 | Stogryn et al. |
| 4,665,195 A | 5/1987 | Stogryn et al. |
| 4,739,051 A | 4/1988 | Schroeder et al. |
| 4,845,218 A | 7/1989 | Schroeder |
| 4,910,304 A | 3/1990 | Fischer et al. |
| 5,463,130 A | 10/1995 | Witzel et al. |
| 5,847,131 A | 12/1998 | Simon et al. |
| 6,187,957 B1 | 2/2001 | Meyer et al. |
| 2003/0089591 A1 | 5/2003 | Wolfert et al. |
| 2003/0089592 A1 | 5/2003 | Wolfert et al. |
| 2007/0232833 A1 | 10/2007 | Haese et al. |
| 2011/0009627 A1 | 1/2011 | Schmidtke et al. |
| 2011/0137029 A1 | 6/2011 | Kubanek et al. |
| 2011/0137030 A1 | 6/2011 | Kubanek et al. |
| 2011/0172430 A1 | 7/2011 | Ernst et al. |
| 2011/0251433 A1 | 10/2011 | Wigbers et al. |
| 2011/0251434 A1 | 10/2011 | Muller et al. |

FOREIGN PATENT DOCUMENTS

| | | |
|---|---|---|
| DE | 2445303 A1 | 4/1976 |
| DE | 3027890 A1 | 3/1982 |
| DE | 19859776 A1 | 6/2000 |
| EP | 0137478 A2 | 4/1985 |
| EP | 0235651 A1 | 9/1987 |
| EP | 440829 A1 | 8/1991 |
| EP | 0514692 A2 | 11/1992 |
| EP | 0599180 A1 | 6/1994 |
| EP | 0673918 A1 | 9/1995 |
| EP | 0816350 A1 | 1/1998 |
| EP | 1312599 A1 | 5/2003 |
| EP | 1312600 A1 | 5/2003 |
| GB | 1512797 A | 6/1978 |
| WO | WO-2005/081778 A2 | 9/2005 |
| WO | WO-2005/082834 A1 | 9/2005 |
| WO | WO-2005/110969 A1 | 11/2005 |
| WO | WO-2007/021462 A2 | 2/2007 |
| WO | WO-2009/092724 A1 | 7/2009 |
| WO | WO-2009153272 A2 | 12/2009 |
| WO | WO-2010012672 A2 | 2/2010 |
| WO | WO-2010/031719 A1 | 3/2010 |
| WO | WO-2010052181 A2 | 5/2010 |
| WO | WO-2010054988 A2 | 5/2010 |
| WO | WO-2010069856 A1 | 6/2010 |
| WO | WO-2010089346 A2 | 8/2010 |
| WO | WO-2010121899 A1 | 10/2010 |
| WO | WO-2010136425 A1 | 12/2010 |
| WO | WO-2010146009 A1 | 12/2010 |
| WO | WO-2011/067199 A1 | 6/2011 |
| WO | WO-2011/067200 A1 | 6/2011 |

OTHER PUBLICATIONS

U.S. Appl. No. 13/112,161, filed May 20, 2011, Bou Chedid et al.
U.S. Appl. No. 61/321,517.
U.S. Appl. No. 61/321,522.
International Search Report for PCT/EP2011/058030, mailed May 18, 2011.

*Primary Examiner* — Brian J Davis
(74) *Attorney, Agent, or Firm* — Novak Druce Connolly Bove + Quigg LLP

(57) ABSTRACT

A process for preparing 2-(2-tert-butylaminoethoxy)ethanol (tert-butylaminodiglycol, TBADG) by reacting diethylene glycol (DG) with tert-butylamine (TBA) in the presence of hydrogen and of a copper catalyst, by effecting the reaction at a temperature in the range from 160 to 220° C. in the presence of a copper- and aluminum oxide-containing catalyst, where the catalytically active material of the catalyst, before the reduction thereof with hydrogen, comprises 20 to 75% by weight of aluminum oxide ($Al_2O_3$),
20 to 75% by weight of oxygen compounds of copper, calculated as CuO, and
$\leq$5% by weight of oxygen compounds of nickel, calculated as NiO.

24 Claims, No Drawings

PROCESS FOR PREPARING 2-(2-TERT-BUTYLAMINOETHOXY)ETHANOL (TERT-BUTYLAMINODIGLYCOL, TBADG)

CROSS-REFERENCE TO RELATED APPLICATIONS

This application claims the benefit of U.S. Provisional Application 61/346,923 filed on May 21, 2010 which is incorporated by reference. This application claims the benefit of U.S. Provisional Application 61/407,467 filed on Oct. 28, 2010 which is incorporated by reference.

BACKGROUND OF THE INVENTION

The present application incorporates the provisional U.S. application 61/346,923 filed May 21, 2010 by reference.

The present invention relates to a process for preparing 2-(2-tert-butylaminoethoxy)ethanol (tert-butylaminodiglycol, TBADG) by reacting diethylene glycol (DG) with tert-butylamine (TBA) in the presence of hydrogen and of a copper catalyst.

One use of the process product is that in gas scrubbing, for example, for the selective separation of acidic gases, for example $H_2S$ from gas streams which comprise mixtures of one or more acidic gases and $CO_2$.

EP 137 478 A2 (BASF AG) relates to a process for preparing N-methylpiperidine or N-methylmorpholine by catalytically aminating pentanediols or diethylene glycol with methylamine in the gas phase over a copper catalyst which has been obtained by heat treatment of a basic copper- and aluminum-comprising carbonate.

EP 235 651 A1 (BASF AG) teaches a process for preparing N-methylpiperazine from diethanolamine and methylamine over metallic catalysts. The reaction is performed in the liquid phase (trickle mode) (page 3 last paragraph). According to the example, a $Cu/Al_2O_3$ catalyst is used.

EP 816 350 A1 (BASF AG) describes processes for preparing N-methylpiperidine and N-methylmorpholine by reacting primary amine with a diol over a copper catalyst which has been obtained by impregnating $SiO_2$ pellets with basic copper carbonate, in the liquid or gas phase.

U.S. Pat. No. 4,739,051 A (BASF AG) teaches the preparation of morpholine and piperidine by reaction of DEG or pentanediol with ammonia under hydrogenation conditions in the gas phase at standard pressure and 200° C. over an unsupported Cu/Ni/Al catalyst with yields of 97 and 95%, respectively.

EP 514 692 A2 (BASF AG) discloses processes for preparing amines from alcohols in the presence of catalysts comprising copper and nickel and zirconium oxide and/or aluminum oxide.

DE 198 59 776 A1 (BASF AG) relates to the preparation of amines by reacting alcohols, or aldehydes or ketones, with amines over a catalyst composed of copper and $TiO_2$, to which metallic copper has been added before the shaping of the catalyst material.

EP 440 829 A1 (U.S. Pat. No. 4,910,304) (BASF AG) describes the amination of diols over copper catalysts, especially the preparation of N-methylpiperidine and N-methylmorpholine by reaction of pentanediol or diethylene glycol (DEG) with methylamine and 45% aqueous KOH solution over an unsupported Cu/Al catalyst at 245° C. and 250 bar. The reaction is performed in the liquid phase (trickle mode) (page 3 last paragraph). Suitable catalysts are the catalysts disclosed in DE 24 45 303 A (BASF AG), which are obtainable by heat treatment of a basic copper- and aluminum-comprising carbonate of the general composition $Cu_mAl_6(CO_3)_{0.5m}O_3(OH)_{m+12}$, where m is any value, including non-integers, from 2 to 6, for example the precipitated copper catalyst disclosed in loc. cit., example 1, which is prepared by treating a solution of copper nitrate and aluminum nitrate with sodium bicarbonate and subsequently washing, drying and heat treating the precipitate.

WO 05/110969 A1 (BASF AG) describes a process for continuously preparing an amine by reacting a primary or secondary alcohol, aldehyde and/or ketone with hydrogen and a nitrogen compound selected from the group of ammonia, primary and secondary amines, at a temperature in the range from 60 to 300° C., in the presence of a copper catalyst, wherein the catalytically active material of the catalyst, before the reduction thereof with hydrogen, comprises 20 to 85% by weight of aluminum oxide ($Al_2O_3$), zirconium dioxide ($ZrO_2$), titanium dioxide ($TiO_2$) and/or silicon dioxide ($SiO_2$), and the reaction is effected in the gas phase isothermally in a tubular reactor.

WO 2010/031719 A1 (BASF SE) relates to a process for continuously preparing an amine by reacting a primary or secondary alcohol, aldehyde and/or ketone with hydrogen and a nitrogen compound selected from the group of ammonia, primary and secondary amines, at a temperature in the range from 60 to 300° C., in the presence of a copper- and aluminum-oxide-containing catalyst, wherein the reaction is effected in the gas phase and the catalytically active material of the catalyst, before the reduction thereof with hydrogen, comprises aluminum oxide and oxygen compounds of copper, and the shaped catalyst body is specified.

U.S. Pat. No. 4,487,967 and U.S. Pat. No. 4,665,195 (both Exxon Res. & Eng. Co.) teach the preparation of sterically hindered amino ether alcohols by reaction of corresponding amines with diethylene glycol or polyalkenyl ether glycols. The selectivity problem in the reaction of TBA with DEG owing to the formation of N-tert-butylmorpholine (TBM) is described (U.S. Pat. No. 4,487,967: column 3). The catalysts used are supported and unsupported metals, including $Ni/Al_2O_3/SiO_2$, Ni—Al, Raney Ni, Raney Cu catalysts. In the case of the copper catalysts mentioned, the TBADG yield is only 6.4% (U.S. Pat. No. 4,487,967, column 6, table 1). In the case of the $Ni/Al_2O_3/SiO_2$ catalyst, the isolated TBADG yield is only 54% (U.S. Pat. No. 4,487,967, column 5, example 1).

WO 07/021,462 A2 (Exxon-Mobil Res. & Eng. Comp.) relates to the use of dialkylamine glycols or monoalkylamine glycol ethers in acid gas scrubbing, and the preparation thereof by aminating corresponding glycols. Page 15 mentions the preparation of TBADG from DEG and TBA over a nickel catalyst in only 30% yield, and also discusses the selectivity problem (cf. the scheme on page 15).

WO 05/081778 A2 (Exxon-Mobil Res. & Eng. Comp.) describes, inter alia, the synthesis of TBADG from DEG and TBA over supported metal catalysts, the support having specific pore sizes, pore distributions and surface areas (BET). Preference is given to using nickel catalysts (page 3, paragraph [0009]). In all examples, unsupported nickel catalysts are used. Illustrative results are:

Example 6c, page 28, run 27: DEG conversion=72%, molar TBADG:TBM ratio=13,

Example 9, page 31, 8 h: DEG conversion=62.5%, molar TBADG:TBM ratio=15, and

Example 12, page 37, #170-8: DEG conversion=51.9%, TBADG:TBM mass ratio=15.8, i.e. molar TBADG:TBM ratio=14.

Since no selectivities are reported here, no yield can be calculated. At a TBADG selectivity of 80% (based on DEG), the TBADG yield in the best example (example 6c, page 28, run 27) would be approx. 57%.

U.S. Pat. No. 4,405,585 (Exxon Res. & Eng. Comp.) describes the use of strongly sterically hindered secondary amino ether alcohols for selective removal of $H_2S$ from a gas comprising $CO_2$ and $H_2S$. Example 1, in column 9, describes the preparation of TBADG from TBA and 2-chloroethoxyethanol.

WO 05/082834 (Exxon-Mobil Res. & Eng. Comp.) describes a process for preparing sterically strongly hindered amino ether alcohols and diaminopolyalkenyl ethers by reaction of a primary amine with polyalkylene glycol at elevated temperature and pressure in the presence of a specific catalyst. The catalyst is characterized in that its preparation involved decomposition of organic metal complexes on a support.

It has been recognized in accordance with the invention that the reaction of DG with TBA over nickel catalysts has the considerable disadvantage from a safety point of view that decomposition products of DG form, which cause a critical situation, for example, in the case of disrupted operation of the reactor (especially power failure). In the amination of DG, for example as a result of decarbonylation, there is enhanced formation of undesired components such as methoxyethanol, methoxyethylamine, methanol, methane (see scheme below). Methoxyethanol is toxic, can be removed from TBADG only with difficulty owing to its physical properties, and can thus lead to problems with regard to specification and product quality.

Accordingly, a process has been found for preparing 2-(2-tert-butylamino-ethoxy)ethanol (tert-butylaminodiglycol, TBADG) by reacting diethylene glycol (DG) with tert-butylamine (TBA) in the presence of hydrogen and of a copper catalyst, which comprises effecting the reaction at a temperature in the range from 160 to 220° C. in the presence of a copper- and aluminum oxide-containing catalyst, where the catalytically active material of the catalyst, before the reduction thereof with hydrogen, comprises
20 to 75% by weight of aluminum oxide ($Al_2O_3$),
20 to 75% by weight of oxygen compounds of copper, calculated as CuO, and
≦5% by weight of oxygen compounds of nickel, calculated as NiO.

DETAILED DESCRIPTION OF THE INVENTION

In the process, the reaction is preferably conducted only up to a DG conversion in the range from 20 to 80%, particularly a DG conversion in the range from 30 to 70%.

Preference is given to effecting the reaction not in purely liquid phase, but in the gas phase or gas/liquid mixed phase. Particular preference is given to effecting the reaction in the gas phase.

In the case of a reaction in the gas/liquid mixed phase, hydrogen ($H_2$) and DG are preferably used in a molar ratio of hydrogen:DG=5 to 50, preferably hydrogen:DG=5 to 30.

In a reaction in the gas phase, hydrogen ($H_2$) and DG are preferably used in a molar ratio of hydrogen:DG=40 to 220, particularly hydrogen:DG=50 to 120.

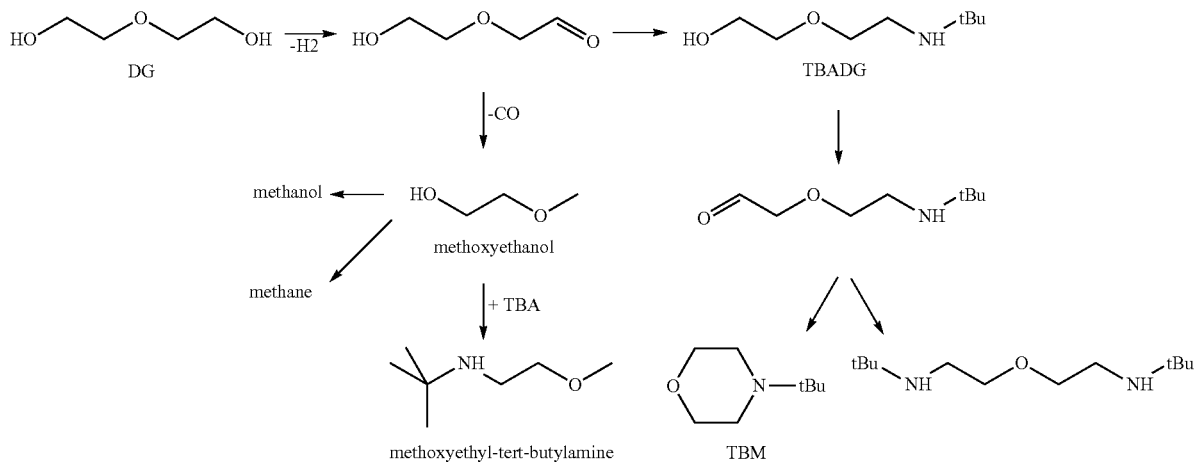

In order to solve this problem, complex specialty reactors are used in some cases; cf., for example WO 2009/092724 A1 (BASF SE), especially page 10, lines 14-21.

BRIEF SUMMARY OF THE INVENTION

It was an object of the invention to remedy the disadvantages of the prior art and to discover an improved economically viable process for preparing TBADG. More particularly, the process should firstly enable high yields, space-time yields (STY) and selectivities and secondly suppress decarbonylation of DG and the associated disadvantages, and hence enable a safe process regime.

[Space-time yields are reported in 'amount of product/(volume of catalyst·time)' ($kg/(l_{cat.} \cdot h)$) and/or 'amount of product/(reactor volume·time)' ($kg/(l_{reactor} \cdot h)$)].

The molar ratio (MR) of hydrogen:DG can be adjusted via the pressure and/or dilution with an inert gas, e.g. $N_2$ or Ar.

Preference is given to effecting the reaction in the absence of a solvent.

In the process according to the invention, the catalysts are preferably used in the form of catalysts which consist only of catalytically active material and optionally a shaping aid (for example, graphite or stearic acid), if the catalyst is used as a shaped body, i.e. do not comprise any further catalytically active accompanying substances.

In this context, the oxidic aluminum oxide ($Al_2O_3$) support material is considered to belong to the catalytically active material.

The catalysts are used in such a way that the catalytically active material is arranged in the reactor after grinding, mixing with shaping aids, shaping and heat treatment in the form of shaped catalyst bodies—i.e. in the form of tablets.

The concentration figures (in % by weight) of the components of the catalyst are based in each case—unless stated otherwise—on the catalytically active material of the finished catalyst after the last heat treatment thereof and before the reduction thereof with hydrogen.

The catalytically active material of the catalyst, after the last heat treatment thereof and before the reduction thereof with hydrogen, is defined as the sum of the masses of the catalytically active constituents and of the abovementioned catalyst support material, and comprises essentially the following constituents:
aluminum oxide ($Al_2O_3$) and oxygen compounds of copper, and preferably oxygen compounds of sodium.

The sum of the abovementioned constituents of the catalytically active material, calculated as $Al_2O_3$, CuO and $Na_2O$, is typically 70 to 100% by weight, preferably 80 to 100% by weight, more preferably 90 to 100% by weight, further preferably 98 to 100% by weight, further preferably ≧99% by weight, most preferably 100% by weight.

The catalytically active material of the catalysts used in the process according to the invention may further comprise one or more elements (oxidation state 0) or the inorganic or organic compounds thereof, selected from groups I A to VI A and I B to VII B and VIII of the Periodic Table.

Examples of such elements and compounds thereof are: transition metals, such as Ni and NiO, Co and CoO, Re and rhenium oxides, Mn and $MnO_2$, Mo and molybdenum oxides, W and tungsten oxides, Ta and tantalum oxides, Nb and niobium oxides or niobium oxalate, V and vanadium oxides or vanadyl pyrophosphate; lanthanides, such as Ce and $CeO_2$ or Pr and $Pr_2O_3$; alkali metal oxides, such as $K_2O$; alkali metal carbonates, such as $Na_2CO_3$; alkaline earth metal oxides, such as CaO, SrO; alkaline earth metal carbonates, such as $MgCO_3$, $CaCO_3$ and $BaCO_3$; boron oxide ($B_2O_3$).

The catalytically active material of the catalysts used in the process according to the invention comprises, after the last heat treatment thereof and before the reduction thereof with hydrogen,
20 to 75% by weight, preferably 25 to 65% by weight, more preferably 30 to 55% by weight, of aluminum oxide ($Al_2O_3$) and
20 to 75% by weight, preferably 30 to 70% by weight, more preferably 40 to 65% by weight, most preferably 45 to 60% by weight, of oxygen compounds of copper, calculated as CuO,
0 to 2% by weight, preferably 0.05 to 1% by weight, more preferably 0.1 to 0.5% by weight, of oxygen compounds of sodium, calculated as $Na_2O$,
≦5% by weight, for example 0.1 to 4% by weight, preferably less than 1% by weight, for example 0 to 0.8% by weight, of oxygen compounds of nickel, calculated as NiO.

The catalytically active material of the catalyst comprises, before the reduction thereof with hydrogen, more particularly less than 1% by weight, for example 0 to 0.5% by weight, of oxygen compounds of cobalt, calculated as CoO.

The catalytically active material of the catalyst used in the process according to the invention most preferably does not comprise any nickel, any cobalt and/or any ruthenium, in each case either in metallic (oxidation state 0) form or in an ionic, especially oxidized, form.

The oxygen compounds of copper are especially copper (I) oxide and copper(II) oxide preferably copper(II) oxide.

The catalytically active material of the catalyst used in the process according to the invention most preferably does not comprise any zirconium dioxide ($ZrO_2$), titanium dioxide ($TiO_2$) and/or silicon dioxide ($SiO_2$).

In a particularly preferred embodiment, the catalytically active material of the catalysts used in the process according to the invention does not comprise any further catalytically active component, either in elemental or in ionic form.

In the particularly preferred embodiment, the catalytically active material is not doped with further metals or metal compounds.

Preferably, however, typical accompanying trace elements which originate from the metal extraction of Cu, and optionally Ni, are excluded therefrom.

For preparation of the catalysts used in the process according to the invention, various processes are possible. They are obtainable, for example by peptizing pulverulent mixtures of the hydroxides, carbonates, oxides and/or other salts of the aluminum, copper and optionally sodium components with water, and subsequently extruding and heat treating the material thus obtained.

The catalysts used in the process according to the invention can also be prepared by impregnating aluminum oxide ($Al_2O_3$), which is present, for example, in the form of powder or tablet moldings.

Aluminum oxide can be used here in different polymorphs, preference being given to α—(alpha), γ—(gamma) or θ-$Al_2O_3$ (theta-$Al_2O_3$). Particular preference is given to using γ-$Al_2O_3$.

Shaped bodies of aluminum oxide can be produced by the customary processes.

The aluminum oxide is likewise impregnated by the customary processes, as described, for example in EP 599 180 A, EP 673 918 A or A. B. Stiles, Catalyst Manufacture—Laboratory and Commercial Preparations, Marcel Dekker, New York (1983), by applying an appropriate metal salt solution in each case in one or more impregnation stages, using, as the metal salts, for example corresponding nitrates, acetates or chlorides. After the impregnation, the material is dried and optionally calcined.

The impregnation can be effected by what is known as "incipient wetness" method, in which the inorganic oxide (e.g. aluminum oxide) is moistened with the impregnating solution up to a maximum of saturation according to its water absorption capacity. The impregnation can, however, also be effected in supernatant solution.

In multistage impregnation processes, it is appropriate to dry and optionally to calcine between individual impregnation steps. Multistage impregnation should be employed advantageously particularly when the inorganic oxide is to be contacted with a relatively large amount of metal.

To apply a plurality of metal components to the inorganic oxide, the impregnation can be effected simultaneously with some or all metal salts, or in any desired sequence of the individual or plural metal salts.

Preference is given to preparing the catalyst used in the process according to the invention by employing precipitation methods. For example, they can be obtained by a coprecipitation of the components from an aqueous salt solution by means of mineral bases in the presence of a slurry of a sparingly soluble oxygen-containing aluminum compound, and then washing, drying and calcining the resulting precipitate. The sparingly soluble oxygen-containing aluminum compound used may, for example, be aluminum oxide. The slurries of the sparingly soluble aluminum compound can be prepared by suspending finely divided powders of this compound in water while stirring vigorously. These slurries are advantageously obtained by precipitating the sparingly soluble aluminum compound from aqueous aluminum salt solutions by means of mineral bases.

Preference is given to preparing the catalysts used in the process according to the invention by means of a co-precipitation precipitation of all components thereof. For this purpose, an aqueous salt solution comprising the catalyst components is appropriately admixed under hot conditions and while stirring with an aqueous mineral base, especially an alkali metal base—for example sodium carbonate, sodium hydroxide, potassium carbonate, or potassium hydroxide— until the precipitation is complete. The type of salts used is generally not critical: since the principle concern in this procedure is the water solubility of the salts, one criterion is the good water solubility thereof, which is required to prepare these comparatively highly concentrated salt solutions. It is considered to be obvious that, in the selection of the salts of the individual components, the salts selected are of course only those with anions which do not lead to disruption, whether by causing undesired precipitation or by complicating or preventing precipitation as a result of complex formations.

The precipitates obtained in these precipitation reactions are generally chemically inhomogeneous and consist, inter alia, of mixtures of the oxides, oxide hydrates, hydroxides, carbonates, and insoluble and basic salts of the metal(s) used. It may be found to be favorable for the filterability of the precipitates when they are aged, i.e. when they are left alone for a certain time after precipitation, optionally under hot conditions, or while passing air through.

The precipitates obtained after these precipitation processes are processed further as usual to give the catalysts used in accordance with the invention. After washing, they are preferably dried at 80 to 200° C., preferably at 100 to 150° C., and then calcined. The calcination is preferably performed at temperatures between 300 and 800° C., preferably 400 to 600° C., especially 450 to 550° C.

After the calcination, the catalyst is appropriately conditioned, whether by adjusting it to a particular particle size by grinding and/or by mixing it, after the grinding thereof, with shaping aids such as graphite or stearic acid, pressing it by means of a press to the moldings, i.e. tablets, and heat treating. The heat treatment temperatures preferably correspond to the temperatures in the calcination.

The catalysts prepared in this way comprise the catalytically active metals in the form of a mixture of the oxygen compounds thereof, i.e. especially as the oxides and mixed oxides.

The catalysts prepared in this way are stored and may be traded as such. Before the use thereof as catalysts, they are typically pre-reduced. They can, however, also be used without pre-reduction, in which case they are reduced by the hydrogen present in the reactor under the conditions of the hydrogenating amination.

For pre-reduction, the catalysts are first exposed to a nitrogen-hydrogen atmosphere at preferably 150 to 200° C. over a period of, for example, 12 to 20 hours, and then treated in a hydrogen atmosphere at preferably 200 to 400° C. for another up to approx. 24 hours. This pre-reduction reduces a portion of the oxygen-containing metal compound(s) present in the catalysts to the corresponding metal(s), such that they are present in the active form of the catalyst together with the different kinds of oxygen compounds.

The catalyst is preferably characterized by a micropore volume of <0.5 cm$^3$/g, particularly <0.4 cm$^3$/g, for example <0.3 cm$^3$/g, (measured to DIN 66135-1). (According to the 1984 IUPAC recommendation, micropores are defined as pores with pore sizes below 2 nm: K. S. W. Sing et al., Pure & Appl. Chem. 57 (1985) 4, 603-619).

In addition, the catalyst is preferably characterized by the following pore size distribution: if normalized to pores with a pore size of >0 to $\leq$20 nm (measured to DIN 66134 (for the mesopores, pore size$\geq$2 to $\leq$20 nm) and DIN 66135-1 (for the micropores)), $\leq$30% of the pores have a pore size up to 5 nm and more than 70% of the pores have a pore size of >5 to 20 nm.

The reaction in the process according to the invention is preferably effected in a tubular reactor.

The reaction in the tubular reactor by the process according to the invention is most preferably effected in a cycle gas mode.

The cycle gas consists of predominantly hydrogen or a mixture of hydrogen and an inert gas (e.g. $N_2$) and serves to evaporate the reactants and/or as a reactant for the amination reaction.

In cycle gas mode, the starting materials (DG, TBA) are preferably evaporated in a cycle gas stream and supplied to the reactor in gaseous form.

The reactant (DG, TBA) can also be evaporated as aqueous solutions and passed on to the catalyst bed with the cycle gas stream.

Examples of suitable reactors with a cycle gas stream can be found in Ullmann's Encyclopedia of Industrial Chemistry, 5th Ed., vol. B 4, pages 199-238, "Fixed-Bed Reactors".

The cycle gas rate is preferably in the range from 40 to 2500 m$^3$ (at operating pressure)/[m$^3$ of catalyst (bed volume)·h], especially in the range from 100 to 2000 m$^3$ (at operating pressure)/[m$^3$ of catalyst (bed volume)·h].

The cycle gas into a gas/liquid mixed phase mode comprises preferably at least 10%, particularly 50 to 100%, and very particularly 80 to 100% by volume of $H_2$.

The cycle gas into a gas phase mode comprises preferably at least 10%, more preferably 20 to 80%, and very particularly 30 to 60% by volume of $H_2$.

The preferably isothermal reaction in the process according to the invention is effected preferably with a temperature deviation of not more than +/−8° C., particularly not more than +/−5° C., especially not more than +/−4° C., very particularly not more than +/−3° C., for example not more than +/−0 to +/−2° C. or not more than +/−0 to +/−1° C.

These temperature deviations relate to the particular temperatures in the particular catalyst bed, specifically on entry of the reactants into the catalyst bed and on exit of the reaction mixture out of the catalyst bed.

It is possible for a plurality of catalyst beds to be connected in parallel or in series. When a plurality of catalyst beds are connected in series, the temperature deviations mentioned in the isothermal method preferred in accordance with the invention relate to the particular temperature in the catalyst bed, specifically on entry of the reactants into the first catalyst bed and on exit of the reaction mixture out of the last catalyst bed.

In a preferred embodiment, the temperature of the reactor tube is controlled externally with a heat carrier stream, in which case the heat carrier may, for example, be an oil, a salt melt or another heat-transferring liquid.

Advantages of the inventive reaction regime over a synthesis in the liquid-only phase and in particular over a non-isothermal synthesis include those of better yields and greater safety with regard to runaway reactions.

As a result of the preferably isothermal gas phase mode or gas/liquid mixed phase mode, preferably gas phase mode, the potential of a runaway reaction during the synthesis is greatly reduced. The material present in the reactor which would be available for a runaway reaction is only a fraction of the material in a liquid phase-only process.

The process according to the invention is preferably performed continuously, in which case the catalyst is preferably arranged as a fixed bed in the reactor. In this case, flow toward the fixed catalyst bed either from above or from below is possible.

TBA and DG are preferably used in a molar ratio of TBA: DG=1 to 4, particularly in a molar ratio of TBA:DG=1 to 3, more particularly in a molar ratio of TBA:DG=1 to 2.

The process according to the invention is preferably performed at an absolute pressure in the range from 1 to 200 bar, preferably 2 to 100 bar, more preferably 3 to 50 bar.

The process according to the invention is preferably performed at a temperature in the range from 165 to 205° C., more preferably 170 to 200° C., further preferably 175 to 195° C.

The catalyst hourly space velocity is preferably in the range from 0.1 to 2.0 kg, preferably 0.1 to 1.0 kg, and more preferably 0.2 to 0.7 kg of DG per liter of catalyst (bed volume) and hour. The use of higher catalyst hourly space velocities is possible.

The pressure in the reactor, which arises from the sum of the partial pressures of the TBA, DG and of the reaction products formed at the given temperatures is appropriately increased by injecting hydrogen to the desired reaction pressure.

The water of reaction formed in the course of the reaction generally does not have a disruptive effect on the conversion, the reaction rate, the selectivity and the catalyst service life, and is therefore appropriately removed therefrom only on workup of the reaction product, for example by distillation.

The excess hydrogen and any excess aminating agent present are removed from the reaction discharge, after it has appropriately been decompressed, and the crude reaction product obtained is purified, for example by a fractional rectification. Suitable workup processes are described, for example, in EP 1 312 600 A and EP 1 312 599 A (both BASF AG).

Unconverted reactants (DG and/or TBA) and also any suitable by-products obtained are more preferably recycled back into the TBADG synthesis. Unconverted TBA can, for example, in batchwise or continuous mode, after condensation of the products in the separator, be passed over the catalyst bed again in the cycle gas stream. Unconverted reactants can also be recycled into the synthesis after one or more continuous or batchwise workup step(s), for example, distillation(s), in pure form or else optionally as a mixture with a suitable secondary component.

All pressure figures relate to the absolute pressure.

EXAMPLES

A series of experiments on the preparation of 2-(2-tert-butylaminoethoxy)ethanol (TBADG) from tert-butylamine (TBA) and diethylene glycol (DG) in the presence of hydrogen was conducted in batchwise and continuous modes. Conditions were selected in order to study the conversions and selectivities in the liquid phase and in the gas phase. The catalyst was in each case first activated and then used. The analysis was performed by means of gas chromatography (GC) on an Rtx-5-Amine column (with length 30 m, internal diameter 0.32 mm, coating 1.5 µm) and with a temperature program of 60° C. to 280° C. at 4° C./min. The quantitative analysis was effected by determining factors for DG, TBADG, N-tert-butylmorpholine (TBM) and 2,2'-di(tert-butylamino)diethyl ether (DAE) with diethylene glycol dimethyl ether (DGDME) as the standard. For technical reasons, it was not possible to analyze the TBA quantitatively (decompression losses). The conversion was calculated based only on the DG.

The results of the experiments are reported in the tables as diethylene glycol conversion (DG conversion) in mol % of the DG used, as the TBADG selectivity (TBADG selectivity) in mol % of the DG converted, as the molar ratio of TBADG to the TBM by-product (TBADG/TBM molar) and as the TBADG yield (calculated from the DG conversion and the TBADG selectivity).

Preparation of the Nickel-Free Catalyst A (A1 and A2)

The nickel-free copper catalyst A possessed the composition of 50% by weight of CuO and 50% by weight of gamma-$Al_2O_3$ (after the last heat treatment thereof and before the reduction thereof with hydrogen). Catalyst A was prepared by coprecipitation of copper oxides and aluminum oxides from the nitrate solution thereof (according to DE 30 27 890 A1, page 14 ff., examples 1 and 2), catalyst A1, or by impregnating gamma-$Al_2O_3$ powder with an aqueous copper nitrate solution, catalyst A2. The tableting was effected in each case by the customary method. Before commencement of the reaction, the catalyst was reduced in a hydrogen stream (see below).

Micropore volume of the catalysts A1 and A2 thus obtained: 0.03 $cm^3/g$.

Pore size distribution in the catalysts A1 and A2 thus obtained: normalized to pores with a pore size of >0 to ≦20 nm (measured to DIN 66134 (for the mesopores, pore size≧2 to ≦20 nm) and DIN 66135-1 (for the micropores)), about 18% of the pores had a pore size of less than 5 nm.

Comparative Example 2 (CE-2)

Batchwise Process in the Mixed Phase

DG (36.3 g, 0.34 mol), TBA (100.0 g, 1.36 mol), and catalyst (5 g, activated comparative catalyst CC1, 28% by weight of Ni as NiO, 13% by weight of Cu as CuO on zirconium dioxide) were initially charged in an autoclave (300 ml). The autoclave was inertized with nitrogen and hydrogen was injected to 50 bar. After heating to 195° C., the pressure was adjusted to 100 bar with hydrogen and, when the pressure decreased during the reaction, hydrogen was injected again to 100 bar. Samples were taken and analyzed by means of GC. The result is entered in table 1, CE-2.

Example 2 (E-2)

Batchwise Process in the Mixed Phase

DG (32.6 g, 0.31 mol), and TBA (90.0 g, 1.23 mol) were initially charged in an autoclave (300 ml) provided with a catalyst basket. The activated catalyst A1 (5 g) was introduced into the catalyst basket and placed into the autoclave. The autoclave was inertized with nitrogen and hydrogen was injected to 50 bar. After heating to 205° C. the pressure was adjusted to 100 bar with hydrogen and, when the pressure decreased during the reaction, hydrogen was injected again to 100 bar. Samples were taken and analyzed by means of GC. The result is entered in table 1, E-2.

Comparative Example 3 (CE-3)

Continuous Process in the Gas Phase

For the continuous preparation of TBADG, TBA and DG were used to prepare a feed mixture in a molar ratio of 2:1.

The amination was performed in an oil-heated jacketed glass reactor (D=40 mm, L=900 mm) with capacity approx. 1000 ml. The reactor was safeguarded to a pressure of 0.2 bar gauge with a glass relief valve, and was operated at standard pressure. The feed was metered in at the top of the upright reactor together with the heated hydrogen by means of a feed pump. As a result of the temperature and the sufficient amount of hydrogen, the feed mixture was evaporated at the top of the reactor and conducted over the catalyst in gaseous form within the reactor. At the reactor outlet at the bottom was a receiver with a jacketed coil condenser, where the starting materials and the products were condensed and collected. The reactor was filled with approx. 200 ml of catalyst and, above that 800 ml of V2A metal rings. The catalyst comprised 46% by weight of Cu as CuO and 11% by weight of Ni as NiO on aluminum oxide, and was reduced before the start of the experiment at 180-200° C. first with a hydrogen/nitrogen mixture and later with pure hydrogen (activation). Then 150 ml/h of the feed mixture (by calculation, 54.2 g/h of DG) and 160 l (STP)/h of hydrogen were fed to the reactor from the top downward at 190° C. The result of the experiment is entered in table 2, CE-3.

[Standard liters (l (STP))=volume converted to standard conditions (20° C., 1 bar)].

Example 5 (E-5)

Continuous Process in the Gas Phase 150 ml/h of a mixture of TBA and DG in a molar ratio of 2:1 and 160 l (STP)/h of hydrogen were fed continuously at standard pressure (1 bar) and 190° C. to 200 ml of catalyst A1 in the same system as in CE-3. Before the start of the experiment, the catalyst was reduced at 180-200° C. first with a hydrogen/nitrogen mixture and later with pure hydrogen (activation). The result is entered in table 2, B-5.

Example 6 (E-6)

Continuous Process in the Gas Phase 150 ml/h of a mixture of TBA and DG in a molar ratio of 3:1 and 160 l (STP)/h of hydrogen were fed continuously at standard pressure (1 bar) and 190° C. to 200 ml of catalyst A1 in the same system as in CE-3. Before the start of the experiment, the catalyst was reduced at 180-200° C. first with a hydrogen/nitrogen mixture and later with pure hydrogen (activation). The result is entered in table 2, B-6.

Examples 7, 8 and 10, 11 (E-7, E-8 and E-10, E-11)

The following series of experiments (E-7 to E-11) was carried out in an oil-heated jacketed V2A reactor (D=6 mm, L=12.5 m) of capacity approx. 350 ml. The feed and the hydrogen were metered in continuously at the top of the upright reactor.

Example 7 (E-7)

Continuous Process in the Mixed Phase 260 ml/h of a mixture of TBA and DG in a molar ratio of 4:1 and 1500 l (STP)/h of hydrogen were conducted continuously at 200 bar and 180° C. to 200 ml of catalyst A1. Before the start of the experiment, the catalyst was reduced at 180-200° C. first with a hydrogen/nitrogen mixture and later with pure hydrogen (activation). The result is entered in table 2, E-7.

Example 8 (E-8)

Continuous Process in the Mixed Phase 260 ml/h of a mixture of TBA and DG in a molar ratio of 4:1 and 1500 l (STP)/h of hydrogen were conducted continuously at 50 bar and 180° C. to 200 ml of catalyst A1. Before the start of the experiment, the catalyst was reduced at 180-200° C. first with a hydrogen/nitrogen mixture and later with pure hydrogen (activation). The result is entered in table 2, E-8.

Example 10 (E-10)

Continuous Process in the Mixed Phase 700 ml/h of a mixture of TBA and DG in a molar ratio of 2:1 and 1500 l (STP)/h of hydrogen were conducted continuously at 25 bar and 185° C. to 200 ml of catalyst A1. Before the start of the experiment, the catalyst was reduced at 180-200° C. first with a hydrogen/nitrogen mixture and later with pure hydrogen (activation). The result is entered in table 2, E-10.

Example 11 (E-11)

Continuous Process in the Mixed Phase 700 ml/h of a mixture of TBA and DG in a molar ratio of 2:1 and 1500 l (STP)/h of hydrogen were conducted continuously at 5 bar and 185° C. to 200 ml of catalyst A1. Before the start of the experiment, the catalyst was reduced at 180-200° C. first with a hydrogen/nitrogen mixture and later with pure hydrogen (activation). The result is entered in table 2, E-11.

Examples 12 to 16 (E-12 to E-16)

In the following series of experiments (E-12 to E-16), the influence of nitrogen together with hydrogen as a carrier gas for the reaction of DG with TBA in the gas phase was studied. The amination was performed in an oil-heated jacketed V2A reactor (D=41.1 mm, L=3500 mm) of capacity approx. 5 l. The feed was metered in at the top of the upright reactor together with the heated hydrogen by means of a feed pump. As a result of the temperature established and the sufficient amount of hydrogen, the feed mixture was evaporated at the top of the reactor and conducted over the catalyst in gaseous form within the reactor. At the reactor outlet was a high-pressure separator at an operating temperature of 40° C., in which the hydrogen was removed from the liquid discharge and circulated by means of a pump back into the oven. Two additional pumps were used to return a particular amount of fresh hydrogen gas and a particular amount of nitrogen to the cycle gas. A pressure-regulating valve regulated the offgas rate; this kept the pressure in the system constant. The reactor was filled with 1 liter of catalyst A1. Before the start of the experiment, the catalyst was reduced at 180-200° C. first with a hydrogen/nitrogen mixture and later with pure hydrogen (activation).

Example 12 (E-12)

Continuous Process in the Gas Phase 3.1 l/h of a mixture of TBA and DG in a molar ratio of 4:1 and 8.3 m$^3$ (STP)/h of hydrogen were fed in continuously at 5 bar and 180° C. with no nitrogen. The hydrogen to diethylene glycol ratio was 56:1, and the residence time approx. 2.5 seconds. The result is entered in table 3, E-12.

[Standard cubic meters (m³ (STP))=volume converted to standard conditions (20° C., 1 bar)].

Example 13 (E-13)

Continuous Process in the Gas Phase 3.1 l/h of a mixture of TBA and DG in a molar ratio of 4:1 and 15.3 m³ (STP)/h of hydrogen were fed in continuously at 10 bar and 180° C. with no nitrogen. The hydrogen to diethylene glycol ratio was 112:1, and the residence time approx. 2.6 seconds. The result is entered in table 3, E-13.

Example 14 (E-14)

Continuous Process in the Gas Phase 2.1 l/h of a mixture of TBA and DG in a molar ratio of 4:1 and 19.3 m³ (STP)/h of hydrogen were fed in continuously at 20 bar and 180° C. with no nitrogen. The hydrogen to diethylene glycol ratio was 217:1, and the residence time approx. 3.8 seconds. The result is entered in table 3, E-14

Example 15 (E-15)

Continuous Process in the Gas Phase 2.1 l/h of a mixture of TBA and DG in a molar ratio of 4:1 and 19.3 m³ (STP)/h of a hydrogen/nitrogen mixture of 1:1 were fed in continuously at 20 bar and 180° C. The hydrogen to diethylene glycol ratio was 107:1, and the residence time approx. 3.9 seconds. The result is entered in table 3, E-15.

Example 16 (E-16)

Continuous Process in the Gas Phase 2.1 l/h of a mixture of TBA and DG in a molar ratio of 4:1 and 19.3 m³ (STP)/h of a hydrogen/nitrogen mixture of 1:1 were fed in continuously at 20 bar and 180° C. The hydrogen to diethylene glycol ratio was 71:1, and the residence time approx. 3.9 seconds. The result is entered in table 3, E-16.
Discussion of Results:

In the presence of a nickel-containing copper catalyst, CE-2 (table 1), the best yield of 42% of TBADG was attained after 8 h, with the best selectivity of 64% at a conversion of 65%. The selectivity at the start (4 h) is good and declines at the end (12 h) the higher the conversion becomes.

In the presence of a nickel-free copper catalyst, example E-2, a yield of 53% was achieved, with a DG conversion of 71% and a selectivity of 74% after 12 h. The selectivity of 74% was not achieved on the nickel-containing catalyst in CE-2.

One advantage of low-nickel, especially nickel-free, copper catalysts is the increase in the yield by approx. 30% by the improvement in the TBADG selectivity by increasing the TBADG/TBM ratio and by reducing the decomposition of DG.

In order to demonstrate the advantage of a nickel-free copper catalyst over a nickel-containing copper catalyst, experiments were also carried out in the gas phase at 1 bar. In comparative example CE-3 (table 2) the reaction was performed on a catalyst comprising 46% by weight of Cu as CuO and 11% by weight of Ni as MO on aluminum oxide, and in example E-5 the reaction was carried out under the same conditions on the nickel-free copper catalyst. The Ni-containing catalyst produces much more of the undesired TBM than the Ni-free catalyst. Even as a result of reduction in the temperature by 10° C. to 180° C. (CE-4), the TBM remains as the main product. On the nickel-free catalyst in E-5, the desired TBADG product is the main product and is produced with a molar ratio to the TBM of approx. 13.3. This is a crucial advantage with regard to material costs.

In the further experiments E-7 to E-11 in table 2, the influence of the pressure on the reaction in a continuous process was studied. Under all conditions in these experiments, a liquid phase and a gaseous phase are present in the reactor. When the pressure is reduced from 200 bar to 50 bar, the yield can be improved from approx. 13% to approx. 32%. The reduction of the pressure further to 25 bar and 5 bar enables a comparable yield of approx. 30% at double the space velocity. The space-time yield can thus be more than doubled by reducing the pressure from 50 bar to 5 bar.

The reduction of the pressure has two effects:
1) the concentration of hydrogen in the system is reduced,
2) more DG and TBA are present in the gas phase.

Another series of experiments (E-12 to E-16) was carried out under particular conditions in order to maintain a single gas phase (and no liquid phase) in the reactor. The cycle gas rate and optionally the space velocity were adjusted in order to prevent the formation of a liquid phase at relatively high pressure.

The first three experiments show how the conversion of DG, the selectivity and yield of TBADG fall, when the pressure is increased from 5 to 10 and 20 bar. This indicates that not only the second effect mentioned above has an influence on the reaction, but also the concentration of hydrogen. More specifically, the concentration of hydrogen in the system can be described as the molar ratio of hydrogen to DG. The molar ratio (MR) of H2 to DG has to be increased in the specific examples at relatively high pressure from approx. 56 to approx. 217, in order to maintain a gas phase system. Experiments E-15 and E-16 were conducted under the same conditions, except that hydrogen has been replaced stepwise with nitrogen. However, the total cycle gas rate was kept constant in order to prevent the formation of a liquid phase. The MR H2:DG was reduced as a result from 217 to 107 and 71. In agreement with the observations so far, the lowering of the MR H2:DG improved the conversion of DG and the selectivity and the yield of TBADG.

TABLE 1

| Experiment | Cat. | Temp. | Pressure | MR TBA:DG | Sample x h | TBADG/TBM (molar) | DG conversion | TBADG selectivity | TBADG yield |
|---|---|---|---|---|---|---|---|---|---|
| CE-2 | CC1 | 195° C. | 100 bar | 4:1 | 4 h | 4.0 | 49% | 63% | 31% |
|  |  |  |  |  | 8 h | 2.9 | 65% | 64% | 42% |
|  |  |  |  |  | 12 h | 1.3 | 85% | 46% | 39% |
| E-2 | Cu/Al₂O₃ | 195° C. | 100 bar | 4:1 | 12 h | 3.3 | 71% | 74% | 53% |

TABLE 2

| Experiment No. | Pressure bar | Temp ° C. | Feed g/h DG | Feed ml/h Total | Space velocity kg/l·h DG | H2 l (STP)/ l·h | MR TBA:DG:H2 | DG conversion mol % | TBADG selectivity mol % | TBADG/TBM ratio (molar) | TBADG yield mol % |
|---|---|---|---|---|---|---|---|---|---|---|---|
| CE-3 | 1 | 190 | 54.2 | 150 | 0.27 | 800 | 2:1:14 | 83.2 | 13.3 | 0.2 | 11.1 |
| CE-4 | 1 | 180 | 54.2 | 150 | 0.27 | 800 | 2:1:14 | 64.6 | 36.1 | 0.8 | 23.3 |
| E-5 | 1 | 190 | 54.2 | 150 | 0.27 | 800 | 2:1:14 | 67.8 | 70.0 | 13.3 | 47.4 |
| E-6 | 1 | 190 | 54.2 | 200 | 0.27 | 800 | 3:1:14 | 71.7 | 84.7 | 13.6 | 60.7 |
| E-7 | 200 | 180 | 50 | 260 | 0.27 | 7500 | 4:1:13 | 15.2 | 89.0 | 11.9 | 13.5 |
| E-8 | 50 | 180 | 50 | 260 | 0.26 | 7500 | 4:1:14 | 40.4 | 78.2 | 4.5 | 31.6 |
| E-10 | 25 | 185 | 130 | 700 | 0.62 | 7500 | 4:1:6 | 30.9 | 84.3 | 6.4 | 26.0 |
| E-11 | 5 | 185 | 130 | 700 | 0.62 | 7500 | 4:1:6 | 38.6 | 78.8 | 5.4 | 30.4 |

TABLE 3

| Exp.. No. | Pressure (bar) | Temp. [° C.] | Feed kg/h DG | Feed l/h tot. | Sp. vel. (kg/l·h) DG | Cycle gas [m³ (STP)/h] | Fresh gas [l (STP)/h] | MR TBA: DG | MR H2: DG | MR N2: H2 | DG conversion mol % | TBADG selectivity mol % | TBADG/TBM ratio molar | TBADG yield mol % |
|---|---|---|---|---|---|---|---|---|---|---|---|---|---|---|
| E-12 | 5 | 180 | 636 | 3.1 | 0.64 | 8 | 300 | 4 | 56 | 0 | 30.0 | 64.8 | 1.9 | 19.4 |
| E-13 | 10 | 180 | 636 | 3.1 | 0.64 | 15 | 300 | 4 | 112 | 0 | 27.1 | 51.0 | 1.1 | 13.8 |
| E-14 | 20 | 180 | 424 | 2.1 | 0.42 | 19 | 300 | 4 | 217 | 0 | 19.7 | 46.0 | 0.9 | 9.0 |
| E-15 | 20 | 180 | 424 | 2.1 | 0.42 | 19 | 300 | 4 | 107 | 1 | 35.4 | 78.3 | 4.2 | 27.7 |
| E-16 | 20 | 180 | 424 | 2.1 | 0.42 | 19 | 300 | 4 | 71 | 2 | 30.3 | 83.4 | 6.2 | 25.2 |

The invention claimed is:

1. A process for preparing 2-(2-tert-butylaminoethoxy) ethanol (tert-butylamino-diglycol, TBADG) by reacting diethylene glycol (DG) with tert-butylamine (TBA) in the presence of hydrogen and of a copper catalyst, which comprises effecting the reaction at a temperature in the range from 160 to 220° C. in the presence of a copper- and aluminum oxide-containing catalyst, where the catalytically active material of the catalyst, before the reduction thereof with hydrogen, comprises
   20 to 75% by weight of aluminum oxide ($Al_2O_3$),
   20 to 75% by weight of oxygen compounds of copper, calculated as CuO, and
   ≦5% by weight of oxygen compounds of nickel, calculated as NiO.

2. The process according to claim 1, wherein the reaction is effected in the gas phase or gas/liquid mixed phase.

3. The process according to claim 1, wherein the reaction is conducted only up to a DG conversion in the range from 20 to 80%.

4. The process according to claim 3, wherein unconverted DG and/or TBA is recycled back into the reaction.

5. The process according to claim 1, wherein the reaction is effected at a temperature in the range from 170 to 205° C.

6. The process according to claim 1, wherein TBA and DG are used in a molar ratio of TBA:DG=1 to 4.

7. The process according to claim 2, wherein hydrogen ($H_2$) and DG are used in a molar ratio of hydrogen:DG=5 to 50 in a reaction in the gas/liquid mixed phase, or in a molar ratio of hydrogen:DG=40 to 220 in a reaction in the gas phase.

8. The process according to claim 1, wherein the catalytically active material of the catalyst, before the reduction thereof with hydrogen, comprises less than 1% by weight of oxygen compounds of nickel, calculated as NiO.

9. The process according to claim 1, wherein the catalytically active material of the catalyst, before the reduction thereof with hydrogen, comprises less than 1% by weight of oxygen compounds of cobalt, calculated as CoO.

10. The process according to claim 1, wherein the catalytically active material of the catalyst, before the reduction thereof with hydrogen, comprises
    25 to 65% by weight of aluminum oxide ($Al_2O_3$) and
    30 to 70% by weight of oxygen compounds of copper, calculated as CuO.

11. The process according to claim 1, wherein the catalytically active material of the catalyst, before the reduction thereof with hydrogen, comprises 0 to 2% by weight of oxygen compounds of sodium, calculated as $Na_2O$.

12. The process according to claim 1, wherein the catalytically active material of the catalyst, before the reduction thereof with hydrogen, comprises 0.05 to 1% by weight of oxygen compounds of sodium, calculated as $Na_2O$.

13. The process according to claim 1, wherein the catalytically active material of the catalyst does not comprise any nickel, cobalt and/or ruthenium.

14. The process according to claim 1, wherein the reaction is effected isothermally, with a temperature deviation of not more than +/−8° C.

15. The process according to claim 1, wherein the reaction is effected in the absence of a solvent.

16. The process according to claim 1, wherein the reaction is effected continuously.

17. The process according to claim 16, wherein the reaction is effected in a tubular reactor.

18. The process according to claim 16, wherein the reaction is effected in a tubular reactor in a cycle gas mode.

19. The process according to claim 18, wherein the cycle gas rate is in the range from 40 to 2500 m³ (at operating pressure)/[m³ of catalyst (bed volume)·h].

20. The process according to claim 18, wherein the cycle gas comprises at least 10% by volume of hydrogen ($H_2$).

21. The process according to claim 1, wherein the reaction is performed at an absolute pressure in the range from 1 to 200 bar.

22. The process according to claim 1, wherein the catalyst is arranged as a fixed bed in the reactor.

23. The process according to claim 1, wherein the reaction is effected in the presence of a catalyst which has a micropore volume of <0.5 cm$^3$/g.

24. The process according to claim 1, wherein the reaction is effected in the presence of a catalyst in which, normalized to pores having a pore size of >0 to 20 nm, ≦30% of the pores have a pore size up to 5 nm and more than 70% of the pores have a pore size of >5 to 20 nm.

\* \* \* \* \*